United States Patent [19]

Miller et al.

[11] Patent Number: 5,096,688
[45] Date of Patent: Mar. 17, 1992

[54] CATALYTIC PROCESS FOR PRODUCING HIGHER ALCOHOLS FROM SYNTHESIS GAS

[75] Inventors: Jeffrey T. Miller, Naperville; Cecelia A. Radlowski, Riverside, both of Ill.

[73] Assignee: Amoco Corporation, Chicago, Ill.

[21] Appl. No.: 365,529

[22] Filed: Jun. 13, 1989

[51] Int. Cl.$^5$ .................... C01B 3/16; C07C 27/06; C07C 29/14

[52] U.S. Cl. .................... 423/437; 423/656; 518/713; 518/717; 568/881; 568/885

[58] Field of Search ............... 518/713, 717; 568/881, 568/885; 423/656, 437

[56] References Cited

U.S. PATENT DOCUMENTS

| | | | |
|---|---|---|---|
| 1,824,896 | 9/1931 | Jaeger | 518/713 |
| 1,868,096 | 7/1932 | Dreyfus . | |
| 1,963,119 | 6/1933 | Dreyfus | 518/717 |
| 2,110,483 | 3/1938 | Guyer | 568/885 |
| 2,241,416 | 5/1941 | Normann | 568/885 |
| 2,685,596 | 8/1954 | Buchmann | 260/449.6 |
| 3,925,490 | 12/1975 | Reich et al. | 568/881 |
| 4,122,110 | 10/1978 | Sugier et al. | 502/307 |
| 4,235,799 | 11/1980 | Wentworth et al. | 260/449.5 |
| 4,346,179 | 8/1982 | Sugier et al. | 518/707 |
| 4,492,773 | 1/1985 | Ball et al. | 518/713 |
| 4,576,968 | 3/1986 | Nay et al. | 518/717 |
| 4,613,707 | 9/1986 | Kouba et al. | 568/881 |
| 4,751,248 | 6/1988 | Lin et al. | 518/707 |
| 4,880,763 | 11/1989 | Eri et al. | 518/717 |
| 5,004,845 | 4/1991 | Bradley et al. | 568/885 |

FOREIGN PATENT DOCUMENTS

| | | | |
|---|---|---|---|
| 738487 | 7/1966 | Canada | 518/713 |
| 707972 | 4/1954 | United Kingdom | 518/717 |

OTHER PUBLICATIONS

Courty et al., *J. Mol. Catalysis*, vol. 17 (1982), pp. 241-254.
Courty et al., *Hydrocarbon Processing* (Nov. 1984), pp. 105-108.
J. M. Moe, "Low Temperature CO Conversion" in *Preprints*, Division of Petroleum Chemistry, ACS, 8, (4) (1963) at B-29 ff.
Newsome, "The Water-Gas Shift Reaction", Catal. Rev.—Sci. Eng., 21, pp. 275-318 (1980).

*Primary Examiner*—Wayne Langel
*Attorney, Agent, or Firm*—Nick C. Kottis; William H. Magidson; Ralph C. Medhurst

[57] ABSTRACT

A two-stage process for converting synthesis gas to higher alcohols includes an alkali metal-containing cobalt synthesis gas conversion catalyst in a first stage and a copper-containing catalyst in a second stage. The process allows great flexibility in selecting the product mix by changing catalyst compositions and process conditions.

48 Claims, No Drawings

CATALYTIC PROCESS FOR PRODUCING HIGHER ALCOHOLS FROM SYNTHESIS GAS

BACKGROUND OF THE INVENTION

1. Field of the Invention

This invention relates generally to synthesis gas conversion and, more specifically, this invention relates to processes for selectively converting synthesis gas to higher alcohols.

2. Brief Description of Related Technology

Large reserves of natural gas or methane are located in remote areas of the world. As oil reserves are depleted, there is great incentive to convert this gas into a commodity liquid fuel. A number of direct methane conversion technologies, such as pyrolysis, oxidative coupling, and direct oxidation exist, but are in the early stages of development. However, there are well-established technologies for the conversion of natural gas into synthesis gas, i.e., a mixture of CO and free hydrogen.

The Fischer-Tropsch process is a well-known synthesis gas reaction for making hydrocarbons. The economics of the Fischer-Tropsch process have been investigated periodically and have generally been found to be unfavorable. The direct synthesis of higher alcohols (i.e., those having 2 or more carbon atoms per molecule) from carbon monoxide and hydrogen has attracted attention because the products are suitable as gasoline extenders and high-octane blending components.

The formation of aliphatic alcohols by the hydrogenation of carbon monoxide is represented by the following equations:

$$2n\, H_2 + n\, CO \longrightarrow C_nH_{2n+1}OH + (n-1)H_2O \quad [1]$$

$$(n+1)\, H_2 + (2n-1)\, CO \longrightarrow C_2H_{2n+1}OH + (n-1)CO_2 \quad [2]$$

The water-gas shift reaction is closely linked to the alcohol synthesis reaction:

$$CO + H_2O \longrightarrow CO_2 + H_2 \quad [3]$$

The hydrogenation of carbon monoxide to hydrocarbons is thermodynamically more favorable than hydrogenation to alcohols; thus, alcohol formation requires selective catalysts in order to minimize hydrocarbon formation.

Catalysts for higher alcohol processes which have reached the commercialization stage or have undergone large-scale pilot plant trials fall into three main categories. They include low temperature methanol synthesis catalysts modified with alkali metals, high temperature methanol synthesis catalysts modified with alkali metals, and modified Fischer-Tropsch catalysts.

Low temperature methanol synthesis catalysts which have been modified for higher alcohol synthesis by the addition of alkali metals usually contain both copper and zinc and may contain oxides of chromium or aluminum. The product of one such catalyst typically contains 50-70 percent methanol depending upon the $H_2/CO$ ratio of the synthesis gas feed, the balance being $C_2$-$C_8$ alcohols and partially hydrogenated oxygenates. The water content can be reduced to a few percent, while the content of light hydrocarbons is negligible. Typical reaction conditions are 1,500 psig and 520° F. The main shortcomings of this type of higher alcohol catalyst include the presence of a high fraction of methanol in the product, sensitivity of the catalyst to the carbon dioxide level, increased light hydrocarbon production, and deterioration of catalyst activity with time, especially when operated at higher temperatures.

High temperature methanol synthesis catalysts which have been modified with alkali metals to produce higher alcohols usually contain ZnO and $Cr_2O_3$ and may also contain oxides of copper. Typical processes of this type operate at $H_2/CO$ ratios of 0.5-3, a temperature of 625°-800° F., a pressure of 1,300-2,600 psig, and a gas hourly space velocity (GHSV) of 3,000-15,000/hr. The alcohol product is about 70 percent methanol, with the remainder being $C_2$-$C_5+$ higher alcohols and oxygenates. Isobutanol is the principal higher alcohol. At these conditions water can be about 20 percent of the crude product, and hydrocarbon contents are low. The catalysts are quite stable with time. Main drawbacks include the presence of a large amount of methanol in the product, the need to remove large amounts of water, the need to use a synthesis gas feed with a low $H_2/CO$ ratio, and a high operating pressure.

One example of a modified Fischer-Tropsch catalyst contains $MoS_2$, CoS, and $K_2O$. This catalyst has been reported to yield about 85 percent mixed alcohols, with the remainder as $C_1$-$C_5$ paraffins.

The crude mixed alcohol product of this type of catalyst contains about 50 percent methanol, with the remainder $C_{2+}$ alcohols and oxygenates. Ethanol is the major higher alcohol. This catalyst effects a water-gas shift reaction at alcohol synthesis conditions and thus provides a product with less than about 3 percent water. One drawback to this process can be a high yield of light hydrocarbons. The catalyst is believed to require 25-50 ppm $H_2S$ in the feed gas to maintain acceptable activity.

The preparation of alcohols from carbon monoxide and hydrogen yields a range of alcohol chain lengths as well as linear or branched alcohols. Generally, higher alcohols which form over copper-containing catalysts are branched; those formed over Group VIII metals are predominantly straight chained.

Mixed copper-cobalt alkalized catalysts have been developed by Institut Francais du Petrole for conversion of synthesis gas to higher alcohols. These catalysts generally also contain aluminum, chromium, and zinc. Although these catalysts contain both copper (a component of many methanol synthesis catalysts) and cobalt (a typical Fischer-Tropsch catalyst component), the product distribution is similar to that obtained from a modified Fischer-Tropsch catalyst, i.e., ethanol is the major $C_{2+}$ alcohol. A typical such catalyst would yield, on a $CO_2$-free basis, 70-80 percent oxygenates and 20-30 percent hydrocarbons. Of the oxygenates, methanol can be 50-70 percent, ethanol 16-25 percent, and the balance other alcohols and partially hydrogenated oxygenates. Such catalysts typically operate at 500 to 600° F., 1000-1500 psig, and a GHSV of 3000-6000/hr, a $H_2/CO$ ratio of 2 or less, and $CO_2$ content in the feed gas of less than 3 percent. Drawbacks include the high methanol fraction in the alcohol product and the large amount of light hydrocarbons that are also produced. The performance of this type of copper-cobalt catalyst is especially sensitive to the method by which it is prepared. Large-scale industrial preparation may need very tight controls to ensure an active material.

SUMMARY OF THE INVENTION

It is an object of the invention to overcome one or more of the problems described above.

According to the invention, a process for converting synthesis gas to alcohols having at least 2 carbon atoms per molecule is provided wherein synthesis gas is contacted with a first, alkali metal- and cobalt-containing synthesis gas conversion catalyst to produce an effluent product containing unconverted synthesis gas, water, and unsaturated organic oxygenates having 2 or more carbon atoms per molecule. The effluent product is then contacted with a second, copper-containing catalyst under conditions whereby at least a portion of the unsaturated organic oxygenates in the effluent are converted to alcohols, and at least a portion of the water present in the effluent is reacted with carbon monoxide in the unconverted synthesis gas to produce carbon dioxide and free hydrogen.

The inventive process provides a relatively dry single phase liquid product which is relatively rich in higher alcohols and relatively lean in methanol and non-alcohol oxygenates.

Other objects and advantages of the invention will be apparent to those skilled in the art from a review of the following detailed description taken in conjunction with the appended claims.

DETAILED DESCRIPTION OF THE INVENTION

According to the invention, higher alcohols (i.e., those containing at least 2 carbon atoms per molecule) may be efficiently produced in high yield from synthesis gas in a two-stage catalytic reaction system. In the inventive system, an alkali metal- and cobalt-containing synthesis gas conversion catalyst converts synthesis gas to linear higher alcohols, preferably with ethanol as the major higher alcohol. The resulting product, which contains a significant amount of water as well as unconverted synthesis gas and unsaturated organic oxygenates in addition to methanol and higher alcohols, is contacted with a copper-containing catalyst in order to upgrade the liquid product by hydrogenating undesirable oxygenates to convert them to higher alcohols and to convert water by reaction with carbon monoxide in the unconverted synthesis gas to produce carbon dioxide and free hydrogen.

The process of the invention is flexible in terms of its ability to be practiced in a single reactor or in multiple reactors, with the two catalyst stages being operated at the same or similar temperatures and pressures, or at different reaction conditions as desired. The composition of the feed synthesis gas can be varied widely, and generally comprises $H_2$ and CO in an $H_2/CO$ molar ratio in the range of about 5:1 to about 1:5, preferably in the range of about 1:1 to about 3:1.

The first reaction stage is preferably carried out at a temperature in the range of about 450° F to about 650° F. and a pressure of at least about 500 psig, preferably at about 1000 to 2500 psig, with the second stage reaction preferably being carried out at a temperature in the range of about 400° F. to about 650° F. and a pressure of at least about 500 psig, preferably at about 1000 to 2500 psig. Preferably, for economic reasons, the reaction stages are carried out at the same or similar pressures, although they may conveniently be carried out at different temperatures, if desired.

At operating conditions, the effluent stream leaving the first reaction zone containing the first catalyst will be gaseous, but will contain condensable components (water, alcohols, etc.). The effluent preferably is fed directly to a second reaction zone containing the second catalyst without intermediate condensation or separation of components, and the reaction over the second catalyst is a gas phase reaction.

A mixed gas/liquid product is obtained by cooling the product of the second reaction to ambient conditions.

The first catalyst functions to at least partially convert synthesis gas to water and unsaturated organic oxygenates having 2 or more carbon atoms per molecule. Preferably, alcohols including higher alcohols are also produced, and hydrocarbons which include olefins and paraffins are generally unavoidably produced as by-products.

As used herein, the term "oxygenates" includes alcohols, and the term "unsaturated oxygenates" denotes non-alcohol oxygenates such as carboxylic acids, aldehydes, ketones, and esters.

An important role of the second catalyst is to convert a portion of the undesirable unsaturated oxygenates to alcohols by hydrogenation and to reduce the water content of the liquid product by means of a water-gas shift reaction.

Descriptions herein of the catalyst-forming components used according to the invention are made with reference to the state of the catalyst prior to reduction under operating conditions unless otherwise specified.

The first catalyst is generally characterized as a catalytically active alkali metal-containing synthesis gas conversion catalyst comprising a major weight proportion (i.e., at least about 50 wt. %) of cobalt (calculated as CoO). The first catalyst may be substantially free of copper, and under operating conditions preferably comprises cobalt metal and oxides (e.g., CoO) modified by the presence of an alkali metal compound, preferably an oxide or carbonate of potassium, sodium, cesium, or rubidium. Preferred alkali metal compounds are $K_2CO_3$ and $Na_2CO_3$.

In a highly preferred form, the alkalized cobalt first catalyst is further modified by the presence of an oxidized transition metal such as zinc oxide (ZnO) or zinc carbonate ($ZnCO_3$).

Cobalt oxide-containing catalysts which are not modified with an alkali metal are effective in converting synthesis gas, but produce a high yield of straight chain, saturated hydrocarbons with only traces of oxygenates. Alkali metal-containing cobalt catalysts, on the other hand, are highly selective for oxygenates, with substantial yields of $C_{2+}$ ("higher") oxygenates. Methanol is the predominant oxygenate in the product.

Since the presence of an alkali metal lowers the activity of cobalt-containing catalysts, relatively high reaction temperatures may be necessary or desirable with alkali metal-containing cobalt synthesis gas conversion catalysts in order to attain acceptable activities.

While the addition of an alkali metal compound to a cobalt-containing synthesis gas conversion catalyst can shift the selectivity of the catalyst from hydrocarbons to a mixture of hydrocarbons and oxygenates, incorporation of a transition metal oxide in addition to the alkali metal promoter can further shift the oxygenate selectivity in favor of higher oxygenates. Zinc oxide is especially preferred as a modifier for shifting the selectivity of the cobalt catalyst to higher alcohols, in particular to ethanol as the major higher oxygenate.

The product of reaction of synthesis gas over a cobalt/zinc oxide/alkali metal catalyst is a complex liquid mixture (at ambient conditions) consisting of two layers, with a relatively dense layer containing mostly water and low molecular weight alcohols, and a less dense layer containing other alcohols along with small amounts of acids, aldehydes, ketones, esters, and saturated hydrocarbons. Ethanol, however, is the predominant single component.

Within the general framework given above, the cobalt-containing catalyst may incorporate a variety of different modifiers and promoters. All such catalysts, however, are very active for conversion of synthesis gas, have good selectivity for higher oxygenates, especially for ethanol, and maintain good long term stability.

For example, a catalyst containing $CoO/ZnO/Al_2O_3/Na_2CO_3$ in a weight ratio of 87/9/4 (on a sodium carbonate-free basis) can withstand sulfide poisoning and still convert synthesis gas to a mixture of hydrocarbons and oxygenates. A $CoO/MnO/ZnO$ catalyst having a weight proportion of 53/40/7 modified with potassium carbonate yields nearly 60 weight percent higher alcohols (on a water-free basis) in a liquid product when operated in a single stage.

Cobalt should be the major catalyst component and the alkali metal and transition metal additives should be present in much smaller amounts in order to maintain high ethanol selectivity compared to methanol, and high activity.

Preferably, the first catalyst should comprise at least about 50 weight percent cobalt (calculated as CoO), up to about 10 weight percent of the alkali metal (calculated as $K_2O$), and 0 to about 20 weight percent of an oxidized transition metal (calculated as ZnO).

The first catalyst is characterized as having a relatively low weight ratio of oxidized transition metal (e.g., zinc) to cobalt, generally in the range of zero to about 0.15, calculated as ZnO/CoO, respectively. Ratios in the range of about 0.08 to about 0.12 are preferred.

Preferably, the first catalyst comprises at least about 0.5 weight percent alkali metal (calculated as $K_2O$) and highly preferably 1 to 5 weight percent alkali metal, calculated as $K_2O$. The first catalyst preferably comprises about 10 weight percent of the oxidized transition metal (calculated as ZnO) and about 90 weight percent cobalt (calculated as CoO), on an alkali metal-free basis.

Additional first catalyst forming materials may include one or more additional metal oxides, such as oxides of titanium, manganese, aluminum, or magnesium, preferably $TiO_2$, $Al_2O_3$, MnO, or MgO. These materials enhance the surface area and physical strength of the catalyst, and may act as a diluent to render the catalyst less active and less expensive.

A highly preferred first catalyst comprises a major weight proportion of cobalt (calculated as CoO) and is prepared by precipitating CoO with subsequent impregnation by an alkali metal compound, or coprecipitation of CoO with an alkali metal compound.

If the cobalt oxide catalyst is to be impregnated with an alkali metal compound, it is first precipitated as part of a non-stoichiometric complex mixture of oxidized cobalt compounds (such as oxides, hydroxides and carbonates, for example), washed, dried, and thereafter impregnated with an aqueous solution of the alkali metal compound and dried to provide a catalytic material. If desired, the dried catalytic material may be calcined prior to use in order to remove any remaining water and to convert remaining cobalt salts to oxide forms which are more readily reduced to metallic cobalt under operating conditions.

Coprecipitation can readily be effected from an aqueous solution of a soluble cobalt salt (e.g., cobalt nitrate) with addition of a soluble alkali metal compound such as sodium or potassium carbonate. The pH is then raised sufficiently to precipitate the mixture of cobalt compounds. A pH of 8-10 is typically sufficiently high to effect precipitation and may be obtained by addition of ammonium hydroxide, for example. The precipitate is washed to remove excess alkali metal and cobalt salt, dried, and optionally calcined. The precipitate must not be washed so thoroughly as to remove all alkali metal, of course.

If a support is desired, it is preferably added after drying of the cobalt oxide precipitate, but can be added with the soluble cobalt salt, if desired.

The second, copper-containing catalyst may be substantially free of cobalt, if desired, and is selected for its ability to hydrogenate unsaturated organic oxygenates and to effect a water-gas shift reaction.

The second catalyst serves to upgrade the product from synthesis gas conversion by the first catalyst. Copper is known to be a hydrogenation catalyst, especially for oxygenates, and the preferred form of copper in the second catalyst is Cu (II) (prior to partial reduction under operating conditions). Although not all copper-containing materials possess the hydrogenation and water-gas shift activities required for use in the invention, copper-containing catalysts which have been found to be useful include those which are active for the synthesis of methanol under the operating conditions of the invention.

The second catalyst can be a member of the methanol synthesis catalyst family or the modified methanol synthesis catalyst family. Typical examples usually contain copper and zinc, but can be ternary mixtures, most commonly Cu-Zn-Cr and Cu-Zn-Al. The modified methanol synthesis catalysts contain alkali metal compounds which serve to suppress methanol synthesis activity.

These catalysts are typically prepared by coprecipitation from an aqueous solution containing Cu(II), Zn(II), and if desired Al(III) or Cr(III) as soluble salts such as nitrates, acetates, citrates, chlorides, etc. Sodium carbonate, potassium carbonate or ammonium carbonate solutions are typically used to coprecipitate the metal ions as carbonates/hydroxides.

In the methanol synthesis catalyst family, the alkali is thoroughly washed out. In the modified methanol synthesis catalyst, the alkali is only partially washed out. Alkali can also be added by impregnation of the dried or calcined metal-containing material with an aqueous alkali metal compound solution.

The Cu/Zn atomic ratio in such catalysts can range about 0.3 to about 2.5. Alumina is considered to be a structural component and can be present in the range of about 2 to 35 mole % as Al. Chromium can be a structural component as well as a catalytic component, and is present typically at about 2 to 35 mole % as Cr.

The alkali metal compound is preferably a carbonate or hydroxide of potassium, sodium, cesium, or rubidium. Alkali metal is not required, however, if the catalyst has low methanol selectivity or if production of substantial amounts of methanol is acceptable.

A preferred copper-containing catalyst is generally characterized as a mixed copper-chrominum oxide which is prepared by coprecipitation with subsequent impregnation with a solution of an alkali metal salt. The coprecipitated mixed copper-chrominum oxide catalyst (with or without alkali) is referred to as a "copper chromite" catalyst.

Preparation of the copper chromite catalyst is preferably effected by coprecipitating copper (II) ions with chromate ions in the presence of an excess of ammonium relative to copper to produce a copper-ammonium-chromate precipitate. Coprecipitation may be conveniently effected by mixing of respective solutions of copper nitrate ($Cu(NO_3)_2$) or another soluble copper (II) salt and a stoichiometric excess of a solution of ammonium chromate (($NH_4)_2CrO_4$) with at least a 3:1 weight ratio of ammonium chromate to copper. If desired, ammonium hydroxide or an equivalent material can be partially substituted for ammonium chromate.

Precipitation of the copper-ammonium-chromate precipitate, which preferably contains a substantially equimolar ratio of chromium to copper, is effected by raising the pH of the mixture, as by the addition of ammonium hydroxide, for example. The equimolar Cu:Cr precipitate is separated from the mixture and dried to produce a brown product.

The copper content of catalysts prepared by precipitation of copper nitrates or similar salts may vary widely, with typical copper contents (calculated as CuO) of about 10 wt. % to 60 wt. %. Copper chromite catalysts made as described above generally contain copper and chromium in a Cu:Cr atomic ratio of about 1:1.5 to about 1.5:1, typically about 1:1 as noted above.

The brown product is then calcined under carefully controlled temperature conditions to produce a stable, black copper chromite catalyst. The calcining step is carried out at a sufficiently high temperature to drive off ammonia and fix the CuO and $Cr_2O_3$ constituents of the copper chromite catalyst. The temperature is controlled so as not to reach a temperature at which the product degrades. A calcining temperature of about 550° F. or less is preferred, although a 600° F. temperature may be used as long as spikes in temperature above 700° F. are avoided. (Slightly higher temperatures may be used if certain other components such as BaO are present.)

After calcining, the black copper chromite catalyst preferably is impregnated with an aqueous solution of a soluble alkali metal compound, and dried to provide an alkali-impregnated copper chromite catalyst. Optionally, the resulting catalyst may be calcined. Temperature control of this calcining step is less important than the initial calcining step and are preferably conducted at temperatures of up to 650° F., such as 625° F.

The alkali metal compound, if present, preferably comprises between about 1 and 10 weight percent of the second catalyst (measured as carbonate) and preferably is present at about a 5 weight percent level.

Of the alkali metals, potassium and sodium are preferred, although cesium and rubidium are acceptable. The alkali metal compound preferably is a potassium salt such as KOH or the highly preferred $K_2CO_3$.

The second catalyst may contain other components, such as zinc, as desired. Barium (in oxide form, BaO) is a useful additional component, especially in copper chromite catalysts. The presence of a soluble barium salt in the catalyst-forming solution facilitates copper chromite precipitation, and results in the formation of stable barium chromite which enhances the physical strength of the catalyst without detrimentally affecting catalyst performance.

In use, the first and second catalysts may be disposed in the same reactor using identical or similar reaction conditions, or different conditions if the reactor design so permits. Alternatively, the catalysts may be disposed in series in separate reactors.

When synthesis gas is passed over the first and second catalyst beds in series, a liquid product is obtained upon cooling of the gaseous effluent, and typically forms a single liquid phase. If synthesis gas is contacted with a first catalyst comprising an alkali metal-containing CoO/ZnO catalyst alone, the reaction would produce a liquid product having an organic phase and an aqueous phase. The production of a single phase establishes that the copper-containing second catalyst effects a water-gas shift reaction.

The alkali metal-containing cobalt catalyst alone typically would yield a lightly colored liquid product which discolors upon contact with air for short time periods. The two catalyst system of the invention, on the other hand, yields optically clear, colorless material which is oxidatively stable when exposed to air over lengthy time periods. This phenomenon may be explained on the basis that copper in the second catalyst hydrogenates constituents in the effluent from the first catalyst which cause color formation upon oxidation.

Gas chromatographic analysis of products from the first catalyst alone and the two catalyst bed product reveals fewer contaminant compounds with the two catalyst system, indicating that the second catalyst is hydrogenating by-product acids, aldehydes, ketones, and esters.

If the effluent from the first reaction stage contains olefins, the second catalyst will be effective in at least partially converting the olefins to paraffins.

EXAMPLES

The following specific examples are provided in order to illustrate the practice of the invention, but are not to be construed to limit the scope of the invention. In the following examples, all percentages are expressed in terms of weight unless specified otherwise.

EXAMPLE 1

In this example, two cobalt catalysts (designated A and B) and two copper catalysts (designated C and D) were prepared and tested for activity as synthesis gas conversion catalysts, both individually and in a tandem catalyst bed process.

The catalyst preparation and alcohol synthesis procedures and results are set forth below.

Catalyst Preparation

Cobalt Catalysts

Catalyst A: 78.32 g of $Ti(OC_3H_7)_4$, titanium tetraisopropoxide, was added to 300 ml of $H_2O$ and stirred. To this mixture was added 230.04 g of $Co(NO_3)_2 \cdot 6H_2O$, 26.28 g $Zn(NO_3)_2 \cdot 6H_2O$, and 4.24 g $K_2CO_3$. The resulting mixture was stirred for approximately one hour. A separately prepared 6M $Na_2CO_3$ solution in water was slowly added until the pH was approximately 10. The resulting solid precipitate was filtered and washed twice, each time with 300 ml $H_2O$. The washed solid was then dried overnight at 250° C. in a vacuum oven. The resulting catalyst was then calcined for two hours at 1200° F. The nominal composition of this catalyst was 67.9% CoO, 20.6% $TiO_2$, 8.2% ZnO, and 3.3% $K_2O$ on a carbonate-free basis. About 5% to 10% residual sodium carbonate remained in the catalyst.

Catalyst B: 318.6 g $Co(NO_3)_2 \cdot 6H_2O$ and 29.2 g $Zn(NO_3)_2 \cdot 6H_2O$ were dissolved in 600 ml $H_2O$. Separately, 200 g $Na_2CO_3$ was dissolved in 600 ml $H_2O$. The $Na_2CO_3$ solution was slowly added to the cobalt solution until the pH was approximately 10. The resulting solid precipitate was filtered and washed twice, each time with 500 ml $H_2O$. The washed solid was dried overnight at 250° F. in a vacuum oven and calcined for two hours at 1200° F. The nominal composition of the catalyst was 91% CoO and 9% ZnO on a carbonate-free basis. Approximately 5% to 10% residual $Na_2CO_3$ remained in the catalyst.

Copper Catalysts

Catalyst C: 26.01 g of $Ba(NO_3)_2$ was dissolved in 800 ml $H_2O$ and heated to 150° F. 218.12 g $Cu(NO_3)_2 \cdot 3H_2O$ was added. A separate solution of ammonium chromate was prepared by dissolving 126.02 g $(NH_4)_2Cr_2O_7$ in 600 ml $H_2O$ and adding 150 ml $NH_4OH$. The two solutions were rapidly mixed. The resulting solid precipitate was filtered and washed twice, each time with 200 ml $H_2O$. The washed solid was dried overnight at 250° F. in a vacuum oven. The resulting catalyst was slowly heated to 600° F. and maintained for one hour. The resulting barium copper chromite catalyst was analyzed to contain 37.6% CuO, 48.2% $Cr_2O_3$, and 8.9% BaO, the balance comprising water, other carbonates, and other oxides.

Catalyst D: To 10 g of Catalyst C was added 0.5 g $K_2CO_3$ dissolved in 7.0 ml $H_2O$. The impregnated catalyst was dried and recalcined for three hours at 600° F. The finished catalyst contained approximately 3.4% $K_2O$.

Testing Procedure

The catalysts were tested for alcohol synthesis in a fixed-bed, continuous-flow pilot plant. Yields were determined by gas chromatography. The flow rate was controlled by mass flow controllers and metered from the test unit by a wet test meter. The gas flow rate (cc of gas per gram of catalyst per hour) and carbon monoxide analysis were determined prior to reaction and again at the reaction temperature. The liquid products were collected for about 24 hours and analyzed by gas chromatography. Liquid samples were tested for water content (percent) by Karl Fischer analysis.

Individual Catalyst Tests

Catalyst A: 5.0 g of Catalyst A was diluted with an equal volume of high surface area carbon and loaded into a fixed bed reactor. The reaction pressure was 1500 psig. The inlet feed gas composition was 44.5 vol. % CO, 7.7 vol. % $CO_2$, and 47.8 vol. % $H_2$. The total gas flow rate was 2392 cc/hr/g catalyst. The reaction temperatures were 575° F. and 590° F., as indicated in Table I. The catalyst was tested for several days at these conditions. The results of the test are summarized in Table I.

The product contained low yields of methanol and high yields of $C_{2+}$ alcohols. Many other oxygenated products were also present. Additionally, the liquid product consisted of two layers, one a predominantly organic (alcohol) layer and one a predominantly water layer. Both layers contained significant levels of both water and alcohols. The water content in the total liquid product was approximately 45 wt. %.

Catalyst B: 5.0 g of Catalyst B was diluted with an equal volume of high surface area carbon and loaded into a fixed bed reactor. The reaction pressure was 1500 psig. The inlet feed gas composition was 46.9 vol. % CO, 8.3 vol. % $CO_2$, and 44.8 vol. % $H_2$. The total gas flow rate was 2399 cc/hr/g catalyst. The reaction temperature was 540° F.

Again the product contained relatively little methanol with high levels of $C_{2+}$ alcohols and other $C_{2+}$ oxygenates. The product also separated into two layers, an aqueous layer and an oxygenate layer. The total liquid product was analyzed to contain approximately 40 wt. % water. Catalyst results are summarized in Table I.

Catalyst C: 3.9 g of Catalyst C (barium copper chromite, a methanol synthesis catalyst) was diluted with an equal volume of high surface area carbon and placed in the fixed bed reactor. The reaction pressure was 1500 psig. The inlet gas composition was H 42.9 vol. % CO, 7.5 vol. % $CO_2$, and 49.6 vol. % $H_2$. The total gas rate was 3251 cc/hr/g/ catalyst. The product was a single layer of nearly pure methanol, although traces of other products were present. The product was analyzed to contain approximately 2 wt. % water. The results of this catalyst test are summarized in Table II.

Catalyst D: 10.0 g of Catalyst D (potassium carbonate promoted barium copper chromite) was diluted with an equal volume of high surface area carbon and placed in the fixed bed reactor. The reaction pressure was 1500 psig. The inlet gas composition was 43.9 vol. CO, 7.7 vol. % $CO_2$, and 48.4 vol. % $H_2$. The total gas flow rate was 1216 cc/hr/g catalyst. This catalyst made mostly methanol, but at a substantially reduced rate compared to Catalyst C. The water in the product was analyzed to be 2.5 wt. %. The catalyst results are summarized in Table II.

Dual Catalyst Tests

Catalyst A followed by Catalyst C: 5.0 g of each catalyst was diluted with an equal volume of high surface area carbon. The catalysts were loaded into the reactor separately such that the temperature of each catalyst could be individually controlled. The effluent contained product from Catalyst A and unconverted synthesis gas, and was passed over Catalyst C. The reaction pressure was 1500 psig. The inlet gas composition was 43.9 vol. % CO, 7.7 vol. % $CO_2$, and 48.4 vol % $H_2$. The total gas flow rate was 1209 cc/hr/g catalyst.

Both catalysts were maintained at the same temperature throughout the test. The reaction temperatures were 550° F., 560° F., and 570° F. Unlike the single catalyst tests for the cobalt higher alcohol catalysts (Catalysts A and B), the product from the two catalysts formed only a single layer. The water content of the total product was reduced to approximately 10 wt. In addition, many of the intermediate oxygenates were hydrogenated to their corresponding alcohols. The yields of $C_{2+}$ alcohols was nearly tripled over those of the single cobalt catalyst tests.

For the two catalyst test, the yield of methanol was also increased compared to that obtained with Catalyst A alone. The yields of methanol can be controlled, however, by selection of process conditions. Finally, although the crude alcohol product from either of the cobalt catalysts alone (Catalyst A or B) changed in color (from colorless to tan) upon standing in air for several days, the product of the two catalyst system was oxidatively stable after several weeks exposure to air. Results are given in Table III.

Catalyst A followed by Catalyst D: 5.0 g of each catalyst was loaded separately into a fixed-bed reactor. The reaction pressure was 1500 psig, and the inlet gas composition was 43.8 vol. % CO, 7.7 vol. % $CO_2$, and 48.5 vol. % $H_2$. The total gas flow rate was 1200 cc/hr/g catalyst. The temperature of the Catalyst A was 560° F. and the temperature of Catalyst D was 545° F. The product formed only a single phase with a water content of approximately 19 wt. %. Because Catalyst D was less active for methanol synthesis relative to Catalyst C, this product was richer, i.e., has a higher selectivity, in $C_{2+}$ alcohols as compared to the test of Catalyst A followed by Catalyst C. While there was 19 wt. % water in the product, this water content was sufficiently low that molecular sieves can be used to dry the final product. The results of this test are given in Table IV.

Catalyst B followed by Catalyst C: 5.0 g of each catalyst was loaded separately to a fixed-bed reactor. The reaction pressure was 1500 psig, and the inlet gas composition was 41.5 vol. % CO, 7.3 vol. % $CO_2$, and 51.2 vol. % $H_2$. The inlet gas flow rate was 1280 cc/hr/g catalyst. The temperature of Catalyst C was maintained at 515° F. and the temperature of Catalyst B was set at 515° F., 540° F., or 545° F. At 515° F. the temperature was too low for Catalyst B to synthesize H many $C_{2+}$ alcohols. The product was mostly methanol, with approximately 10 vol. % $C_{2+}$ alcohols, and contained 3.4 wt. % water. At 540° F., Catalyst B was highly active and the product contained 30% $C_{2+}$ alcohols.

This product contained low levels of water (4.7 wt. %). As shown in Table I, the alcohol product from Catalyst B alone would contain approximately 40 vol. % water.

When Catalyst B was operated at 545° F., $C_{2+}$ alcohol yields and selectivities were increased and the water levels in the product remained low at 5.3 wt. %. The results for this test are given in Table V.

This example demonstrates that copper chromite catalysts can be used to catalytically dry higher alcohol products. In addition, by changes in catalyst composition, loadings, or process conditions, the yields and selectivity of methanol can be adjusted over a wide range. For example, at lower reaction pressures, catalytic drying with copper chromite might be effected without significant increases in the yields of methanol. Also, although these tests were conducted in a single reactor, multi-reactor or multi-stage processing would also be effective.

TABLE I

| Catalyst: | A | | B |
|---|---|---|---|
| Catalyst Components: | $CoO-TiO_2-ZnO-K_2O$ | | $CoO-ZnO-K_2O$ |
| Temperature, °F. | 575 | 590 | 540 |
| Pressure, psig | 1500 | 1500 | 1500 |
| CO Conversion, % | 14.2 | 13.3 | 16.5 |
| Selectivity: | | | |
| (%) $CO_2$ | 44.4 | 42.1 | 41.4 |
| $CH_4$ | 10.5 | 10.1 | 12.2 |
| $C_{2+}$ Hydrocarbons | 18.7 | 19.7 | 16.6 |
| MeOH | 0.9 | 2.6 | 1.4 |
| $C_{2+}$ Alcohols | 7.7 | 11.7 | 14.5 |
| Other | 18.0 | 13.8 | 14.0 |
| Yields (g/hr/g catalyst) | | | |
| $CH_4$ | .011 | .010 | .016 |
| $C_{2+}$ Hydrocarbons | .018 | .017 | .019 |
| MeOH | .0018 | .0049 | .0037 |
| $C_{2+}$ Alcohols | .010 | .014 | .024 |
| % $C_{2+}$ Alcohols in Organic Phase of Liquid | 28.9 | 41.1 | 48.4 |
| % Water in Total Liquid | 45% | 45% | 40% |

TABLE II

| Catalyst: | C | D |
|---|---|---|
| Catalyst Components: | $CuO-Cr_2O_3-BaO$ | $CuO-Cr_2O_3-BaO-K_2O$ |
| Temperature, °F. | 515 | 520 |
| Pressure, psig | 1500 | 1500 |
| CO Conversion, % | 18.7 | 6.1 |
| Selectivity: | | |
| (%) $CO_2$ | — | 1.3 |
| $CH_4$ | 1.4 | — |
| $C_{2+}$ Hydrocarbons | 3.3 | — |
| MeOH | 93.2 | 96.8 |
| $C_{2+}$ Alcohols | .9 | 1.7 |
| Other | 3.7 | .3 |
| Yields (g/hr/g catalyst) | | |
| $CH_4$ | .0026 | — |
| $C_{2+}$ Hydrocarbons | .0013 | — |
| MeOH | .348 | .045 |
| $C_{2+}$ Alcohols | .0022 | .0005 |
| % $C_{2+}$ Alcohols in Organic Phase of Liquid | .9 | 1.7 |

TABLE II-continued

| Catalyst: | C | D |
|---|---|---|
| Catalyst Components: | CuO—Cr$_2$O$_3$—BaO | CuO—Cr$_2$O$_3$—BaO—K$_2$O |
| % Water in Total Liquid | 1.5% | 2.5% |

TABLE III

| Catalysts: | A | and | C |
|---|---|---|---|
| Catalyst Components: | CoO—TiO$_2$—ZnO—K$_2$O | | CuO—Cr$_2$O$_3$—BaO |
| Temperature, °F. | 550 | 560 | 570 |
| Pressure, psig | 1500 | 1500 | 1500 |
| CO Conversion, % | 51.9 | 53.5 | 56.4 |
| Selectivity: | | | |
| (%) CO$_2$ | 30.1 | 36.2 | 40.8 |
| CH$_4$ | 7.7 | 9.9 | 10.7 |
| C$_{2+}$ Hydrocarbons | 8.8 | 12.5 | 13.4 |
| MeOH | 25.3 | 15.9 | 10.5 |
| C$_{2+}$ Alcohols | 19.2 | 18.0 | 18.1 |
| Other | 8.9 | 7.5 | 6.5 |
| Yields (g/hr/g catalyst) | | | |
| CH$_4$ | .015 | .020 | .023 |
| C$_{2+}$ Hydrocarbons | .015 | .022 | .025 |
| MeOH | .100 | .065 | .045 |
| C$_{2+}$ Alcohols | .047 | .046 | .048 |
| % C$_{2+}$ Alcohols in Organic Phase of Liquid | 36.0 | 43.4 | 51.6 |
| % Water in Total Liquid | 10.7 | 10.7 | 9.2 |

TABLE IV

| Catalyst Number: | A | and | D |
|---|---|---|---|
| Catalyst Components: | CoO—TiO$_2$—ZnO—K$_2$O | | CuO—Cr$_2$O$_3$—BaO—K$_2$O |
| Temperature, °F. | | 560/545 | |
| Pressure, psig | | 1500 | |
| CO Conversion, % | | 43.3 | |
| Selectivity: | | | |
| (%) CO$_2$ | | 47.4 | |
| CH$_4$ | | 14.1 | |
| C$_{2+}$ Hydrocarbons | | 16.7 | |
| MeOH | | 1.1 | |
| C$_{2+}$ Alcohols | | 15.3 | |
| Other | | 8.9 | |
| Yields (g/hr/g catalyst) | | | |
| CH$_4$ | | .025 | |
| C$_{2+}$ Hydrocarbons | | .026 | |
| MeOH | | .004 | |
| C$_{2+}$ Alcohols | | .028 | |
| % C$_{2+}$ Alcohols in Organic Phase in Liquid | | 55.6 | |
| % Water in Total Liquid | | 19.7% | |

TABLE V

| Catalyst: | B | and | C |
|---|---|---|---|
| Catalyst Components: | CoO—ZnO—K$_2$O | | BaO—CuO—Cr$_2$O$_3$ |
| Temperature, °F. | 515 | 540/515 | 545/515 |
| Pressure, psig | 1500 | 1500 | 1500 |
| CO Conversion, % | 26.3 | 43.0 | 46.0 |
| Selectivity: | | | |
| (%) CO$_2$ | 24.1 | 36.8 | 40.1 |
| CH$_4$ | 5.1 | 9.1 | 11.1 |
| CH$_{2+}$ Hydrocarbons | 8.3 | 12.1 | 13.0 |
| MeOH | 46.8 | 19.0 | 16.9 |
| C$_{2+}$ Alcohols | 7.4 | 12.9 | 15.5 |
| Other | 8.4 | 10.1 | 3.4 |
| Yields (g/hr/g catalyst) | | | |
| CH$_4$ | .0051 | .015 | .019 |
| C$_{2+}$ Hydrocarbons | .0072 | .017 | .020 |
| MeOH | .093 | .062 | .059 |
| C$_{2+}$ Alcohols | .0093 | .026 | .034 |
| % C$_{2+}$ Alcohols in Organic Phase of Liquid | 11.8 | 30.7 | 43.2 |
| % Water in Total Liquid | 3.4 | 4.7 | 5.3 |

EXAMPLE 2

In this example, a cobalt catalyst (designated E) and a copper catalyst (designated F) were prepared. Catalyst F. was tested for activity as a synthesis gas conversion catalyst, both individually and in a tandem catalyst bed process with Catalyst E.

The catalyst preparation procedure for Catalyst E and alcohol synthesis procedure and results are set forth below.

Catalyst Preparation

Cobalt Catalyst E

A solution of 398.3 g of $Co(NO_3)_2 \cdot 6H_2O$ in 350 ml of $H_2O$ and a solution of 36.5 g $Zn(NO_3)_2 \cdot 6H_2O$ in 50 ml $H_2O$ were added to a beaker and heated to 140° F. with stirring. A solution of 265 g $Na_2CO_3$ in 700 ml $H_2O$ was heated separately to 140° F., and added quickly to the cobalt-zinc solution. Rapid bubbling of gas occurred. The mixture was stirred one additional hour, then allowed to stand for about one hour. The final pH was 9. The mixture was filtered, and the resulting purple solid filter cake was reslurried with 1000 ml $H_2O$ and filtered.

Three days later, the filter cake was reslurried with 500 ml $H_2O$, filtered and dried overnight in a vacuum oven at 100° C.

The resulting dried powder was then calcined at 1100° F. for 4½ hours. The pore volume of the resulting catalyst was 0.52 ml $H_2O$/g catalyst.

22.65 g of the catalyst was subsequently dried and calcined, ground to a fine powder, and impregnated with a solution of 0.82 g $K_2CO_3$ in 12 ml $H_2O$. The resulting impregnated catalyst was dried in a vacuum oven at 106° C. and calcined at 1100° F. for 2 hours.

Catalyst E comprised Co, Zn, and $K_2CO_3$ in a nominal weight ratio of 88/9/3, with Co and Zn measured as CoO and ZnO, respectively.

Catalyst F

This catalyst was a methanol synthesis catalyst obtained from United Catalysts, Inc. of Louisville, KY, under the designation "Alkanols Synthesis Catalyst L-2639" and as delivered contained Cu, Zn, Al, all in oxide form, and alkali metal, in unknown proportions. The catalyst was further impregnated with $K_2CO_3$ to a final catalyst $K_2CO_3$ content of about 12 wt. %.

Catalyst F. was tested individually and in tandem with Catalyst E for alcohol synthesis using the procedure of Example 1, above. Results are set forth below.

Individual Catalyst Test

Catalyst E

This catalyst was not tested individually, but would be expected to perform similarly to Catalyst G, described in Example 3.

Catalyst F 18.85 g of Catalyst F. was loaded into a fixed bed reactor, as in Example 1, and tested for conversion of synthesis gas. The reaction pressure was 2000 psig and the reaction temperature was 550° F. The inlet feed gas composition was 44.3 vol. % CO, 8.0 vol. % $CO_2$, and 47.8 vol. % $H_2$. The inlet gas flow rate was 335 cc/hr/g catalyst. The results of the test are summarized in Table VI, below.

TABLE VI

| Catalyst: | F |
|---|---|
| Catalyst Components: | Cu—Zn—Al-12% $K_2CO_3$ |
| Temperature, °F. | 550 |
| Pressure, psig | 2000 |
| CO Conversion, % | 9.5 |
| Selectivity | |
| (%) $CO_2$ | 0.5 |
| $CH_4$ | 2.9 |
| $C_2^+$ Hydrocarbons | 3.0 |
| MeOH | 62.8 |
| $C_2^+$ Alcohols | 17.4 |
| Other | 13.4 |
| Yields (g/hr/g catalyst) | |
| $CH_4$ | 0.0003 |
| $C_2^+$ Hydrocarbons | 0.0003 |
| MeOH | 0.013 |
| $C_2^+$ Alcohols | 0.002 |
| $C_2^+$ Alcohols in Organic Phase of Liquid | 19 |

Dual Catalyst Test—Catalyst E followed by Catalyst F 7.81 g of Catalyst E and 5.03 g of Catalyst F were loaded into a reactor using the procedure of Example 1. The reaction pressure was 1500 psig, the temperature of Catalyst E was 520° F., and the temperature for Catalyst F was 500° F. The inlet gas composition was 34.0 vol. % CO, 6.1 vol. % $CO_2$, and 60.0 vol. % $H_2$. The inlet gas flow rate was 928.7 cc/hr/g catalyst.

Unlike the single catalyst test for Catalyst E, the liquid product from the two catalysts formed only a single layer.

Results are summarized in Table VII.

TABLE VII

| Catalysts: | E | and | F |
|---|---|---|---|
| Catalyst Components: | CoO—ZnO—$K_2CO_3$ | | Cu—Zn—Al-12% $K_2CO_3$ |
| Temperature, °F. | 520 | | 500 |
| Pressure, psig | | 1500 | |
| CO Conversion, % | | 14.9 | |
| Selectivity: | | | |
| (%) $CO_2$ | | 50.7 | |
| $CH_4$ | | 11.6 | |
| $CH_{2+}$ Hydrocarbons | | 17.5 | |
| MeOH | | 2.8 | |
| $C_{2+}$ Alcohols | | 9.2 | |
| Other | | 7.4 | |
| Yields (g/hr/g catalyst) | | | |
| $CH_4$ | | 0.004 | |
| $C_{2+}$ Hydrocarbons | | 0.005 | |
| MeOH | | 0.002 | |
| $C_{2+}$ Alcohols | | 0.004 | |
| % $C_{2+}$ Alcohols in | | 47.5 | |

TABLE VII-continued

| Catalysts: | E | and | F |
|---|---|---|---|
| Catalyst Components: | CoO—ZnO—$K_2CO_3$ | | Cu—Zn—Al-12% $K_2CO_3$ |
| Organic Phase of Liquid | | | |

EXAMPLE 3

In this example, a cobalt catalyst (designated G) and a copper catalyst (designated H) were tested for activity as synthesis gas conversion catalysts, both individually and in a tandem catalyst bed process.

The catalyst preparation procedure for Catalyst G and alcohol synthesis procedures and result are set forth below.

Catalyst Preparation—Catalyst G

Solutions of 398.3 g of $Co(NO_3)_2 \cdot 6H_2O$ in 350 ml $H_2O$, and 36.5 g $Nz(NO_3)_2 \cdot 6H_2O$ in 50 ml distilled $H_2O$ were separately prepared. The two solutions were added to a beaker and stirred. A solution of 250 g $Na_2CO_3$ in 700 ml distilled $H_2O$ was slowly added to the cobalt-zinc solution and stirred for about 1 hour, and filtered with #3 filter paper.

The filter cake was reslurried twice, each time with 1000 ml $H_2O$ and filtered.

The resulting catalyst was dried in a vacuum oven overnight and then placed in a dessicator.

The resulting catalyst was then calcined, and the pore volume was determined to be 0.31 ml $H_2O$/g catalyst. The catalyst comprised CoO and ZnO in approximate 91/9 weight proportion, and $Na_2CO_3$.

Copper Catalyst

This catalyst was a methanol synthesis catalyst obtained from United Catalysts, Inc. of Louisville, KY under the designation "Alkanols Synthesis Catalyst L-2639" and comprised copper, zinc, copper, and aluminum, all in oxide form, and alkali metal, in unknown proportions.

Testing Procedure

The catalysts were tested for alcohol synthesis in a fixed bed, continuous flow pilot plant using the procedure of Examples 1 and 2 above.

Individual Catalyst Tests

Catalyst G 5.0 g of Catalyst G was loaded into a fixed bed reactor, and tested at a pressure of 1580 psig, and a temperature of 540° F. The synthesis gas feed was 30.7 vol. % CO, 5.4 vol. % $CO_2$, and 63.9 vol. % $H_2$. The inlet gas flow rate was 2447.0 cc/hr/g catalyst. Results are summarized in Table VIII, below.

TABLE VIII

| Catalyst: | G |
|---|---|
| Catalyst Components: | CoO—ZnO—$Na_2CO_3$ |
| Temperature, °F. | 540 |
| Pressure, psig | 1580 |
| CO Conversion, % | 30.5 |
| Selectivity: | |

TABLE VIII-continued

| Catalyst: | G |
|---|---|
| Catalyst Components: | CoO—ZnO—$Na_2CO_3$ |
| (%) $CO_2$ | 38.9 |
| $CH_4$ | 12.9 |
| $C_2^+$ Hydrocarbons | 15.9 |
| MeOH | 2.6 |
| $C_2^+$ Alcohols | 17.8 |
| Other | 11.8 |
| Yields (g/hr/g catalyst) | |
| $CH_4$ | 0.021 |
| $C_2^+$ Hydrocarbons | 0.023 |
| MeOH | 0.009 |
| $C_2^+$ Alcohols | 0.06 |
| % $C_2^+$ Alcohols in Organic Phase of Liquid | 55 |
| $C_2^+$ Olefins/$C_2^+$ paraffins | 0.91 |

Catalyst H

Synthesis gas was passed over Catalyst H alone at pressures of about 1500 psig and 1200 psig at temperatures of about 480° F. and 575° F., respectively.

At 480° F., the feed gas at the reactor inlet contained 33.6 vol. % CO, 6.0 vol. % $CO_2$, and 60.4 vol. % $H_2$. The feed gas used at 575° F. contained 44.1 vol. % CO, 8.2 vol. % $CO_2$, and 47.7 vol. % $H_2$.

The gas flow rate at 480° F. was 2687 cc/hr/g catalyst, and that at 575° F. was 264 cc/hr/g catalyst.

Results are set forth in Table IX, below.

TABLE IX

| Catalyst: | H | |
|---|---|---|
| Catalyst Components: | Cu—Zn—Al-Alkali Metal | |
| Temperature, °F. | 480 | 575 |
| Pressure, psig | 1500 | 2000 |
| CO Conversion, % | 23.7 | 41.3 |
| Selectivity | | |
| (%) $CO_2$ | — | 13.0 |
| $CH_4$ | — | 5.9 |
| $C_2^+$ Hydrocarbons | — | 2.5 |
| MeOH | 98.9 | 62.6 |
| $C_2^+$ Alcohols | 0.2 | 7.3 |
| Other | 0.8 | 6.9 |
| Yields (g/hr/g catalyst) | | |
| $CH_4$ | — | 0.002 |
| $C_2^+$ Hydrocarbons | — | 0.0008 |
| MeOH | 0.30 | 0.04 |
| $C_2^+$ Alcohols | 0.0004 | 0.003 |

Dual Catalyst Test 5.0 g of each catalyst was loaded separately into a reactor, and testing was carried out in the pressure of 1500 psig. Catalyst G was maintained at 500° F. and Catalyst H was maintained at 480° F.

The inlet gas composition was 45.7 vol. % CO, 8.2 vol. % $CO_2$, and 45.1 vol. % $H_2$. The total gas flow rate at the inlet was 1207.0 cc/hr/g catalyst.

Results are set forth in Table X, below.

TABLE X

| Catalyst: | G | and | H |
|---|---|---|---|
| Catalyst Components: | CoO—ZnO—$Na_2CO_3$ | | Cu—Zn—Al-Alkali Metal |
| Temperature, °F. | 500° F. | | 480° F. |
| Pressure, psig | | 1500 | |

TABLE X-continued

| Catalyst:<br>Catalyst Components: | G<br>CoO—ZnO—Na$_2$CO$_3$ | and | H<br>Cu—Zn—Al-Alkali Metal |
|---|---|---|---|
| CO Conversion, % | 20.6 | | |
| Selectivity: | | | |
| (%) CO$_2$ | 42.7 | | |
| CH$_4$ | 7.9 | | |
| CH$_{2+}$ Hydrocarbons | 14.1 | | |
| MeOH | 8.1 | | |
| C$_{2+}$ Alcohols | 12.7 | | |
| Other | 13.6 | | |
| Yields (g/hr/g catalyst) | | | |
| CH$_4$ | 0.006 | | |
| C$_{2+}$ Hydrocarbons | 0.010 | | |
| MeOH | 0.013 | | |
| C$_{2+}$ Alcohols | 0.013 | | |
| % C$_{2+}$ Alcohols in Organic Phase of Liquid | 40.0 | | |

The foregoing detailed description is given for clearness of understanding only, and no unnecessary limitations should be understood therefrom, as modifications within the scope of the invention will be apparent to those skilled in the art.

We claim:

1. A process for converting synthesis gas comprising a mixture of H$_2$ and CO to alcohols having at least 2 carbon atoms per molecule, said process comprising the steps of:
   (a) contacting said synthesis gas with a first catalyst comprising an active alkali metal-containing synthesis gas conversion catalyst comprising a major weight proportion of cobalt (calculated as CoO) under synthesis gas conversion conditions to produce an effluent comprising unconverted synthesis gas, water, and unsaturated organic oxygenates having two or more carbon atoms per molecule; and,
   (b) contacting said effluent with a substantially cobalt-free second catalyst comprising a copper-containing hydrogenation catalyst having water-gas shift activity under selective hydrogenation conditions including a temperature of at least about 400° F. such that at least a portion of said unsaturated organic oxygenates is converted to alcohols and at least a portion of said water is reacted with carbon monoxide in said unconverted synthesis gas to produce carbon dioxide and free hydrogen.

2. The process of claim 1 wherein said first catalyst is substantially free of copper.

3. The process of claim 1 wherein said first catalyst comprises oxidized and metallic cobalt and an alkali metal compound under operating conditions.

4. The process of claim 3 wherein said alkali metal is present in the form of a compound selected from the group consisting of oxides, hydroxides, and carbonates of an alkali metal selected from the group consisting of potassium, sodium, cesium and rubidium, prior to reduction at operating conditions.

5. The process of claim 4 wherein said alkali metal compound is selected from the group consisting of K$_2$CO$_3$ and Na$_2$CO$_3$.

6. The process of claim 3 wherein said first catalyst further contains a minor amount of an oxidized transition metal under operating conditions.

7. The process of claim 6 wherein said oxidized transition metal is selected from the group consisting of ZnO and ZnCO$_3$.

8. The process of claim 4 wherein said first catalyst is prepared by a method comprising the steps of precipitating said oxidized cobalt as part of a non-stoichiometric complex mixture of one or more of the group consisting of cobalt oxides, hydroxides, and carbonates, washing and drying the resulting precipitate, thereafter impregnating said precipitate with a solution of said alkali metal compound, drying and optionally calcining said impregnated precipitate to provide a catalytic material.

9. The process of claim 4 wherein said first catalyst is prepared by a method comprising the step of co-precipitating said oxidized cobalt with said alkali metal compound, followed by washing and drying the resulting precipitate to provide a catalytic material.

10. The process of claim 8 or 9 wherein said first catalyst comprises from about 50 wt.% to less than 100 wt.% oxidized cobalt (calculated as CoO), 0 to about 20 wt.% oxidized zinc (calculated as ZnO), and up to about 10 wt.% of said alkali metal compound (calculated as the oxide), said percentages being based on the total of said oxidized cobalt, oxidized zinc, and alkali metal compound prior to reduction under operating conditions.

11. The process of claim 10 wherein said first catalyst comprises at least about 0.5 wt.% of said alkali metal compound (calculated as the oxide).

12. The process of claim 10 wherein the weight ratio of said zinc to said cobalt is in the range of 0 to about 0.15, calculated as ZnO and CoO, respectively.

13. The process of claim 12 wherein said first catalyst comprises between about 5 wt.% and 15 wt. zinc (calculated as ZnO).

14. The process of claim 1 wherein said second catalyst is effective as a methanol synthesis catalyst, and further comprises an alkali metal compound.

15. The process of claim 1 wherein said second catalyst additionally comprises ZnO.

16. The process of claim 1 or 14 wherein said second catalyst comprises up to about 10 wt.% of an alkali metal compound.

17. The process of claim 1 wherein said synthesis gas comprises H$_2$ and CO in a molar ratio in the range of about 5:1 to about 1:5.

18. The process of claim 17 wherein said H$_2$/CO molar ratio is in the range of about 1:1 to about 3:1.

19. The process of claim 1 wherein said step (a) is carried out at a temperature in the range of about 450° F. to about 650° F. and a pressure of at least about 500 psig.

20. The process of claim 1 wherein said step (b) is carried out at a temperature in the range of about 400° F. to about 650° F. and a pressure of at least about 500 psig.

21. The process of claim 1 wherein said effluent from step (a) further comprises olefins which are converted to paraffins in step (b).

22. A process for converting synthesis gas comprising a mixture of $H_2$ and CO to alcohols having at least 2 carbon atoms per molecule, said process comprising the steps of:
   (a) contacting said synthesis gas with a first catalyst comprising an active alkali metal-containing synthesis gas conversion catalyst comprising a major weight proportion of oxidized and metallic cobalt (calculated as CoO) and a minor amount of an oxidized zinc compound under synthesis gas conversion conditions including a temperature of at least about 450° F. and a pressure of at least about 500 psig to produce an effluent comprising unconverted synthesis gas, water, and unsaturated organic oxygenates having two or more carbon atoms per molecule, said first catalyst comprising from about 50 wt.% to less than 100 Wt.% cobalt (calculated as CoO), 0 to about 20 wt.% oxidized zinc (calculated as ZnO), and up to about 10 wt.% of a first alkali metal compound (calculated as the oxide), the weight ratio of zinc to cobalt being in the range of 0 to about 0.15, calculated as ZnO and CoO, respectively, said percentages being based on the total of said oxidized cobalt, oxidized zinc, and said first alkali metal compound prior to reduction under operating conditions; and
   (b) contacting said effluent with a substantially cobalt-free second catalyst comprising an alkali metal- and copper-containing catalyst having hydrogenation and water-gas shift activity under selective hydrogenation conditions including a temperature of at least about 400° F. and a pressure of at least about 500 psig such that a portion of said unsaturated organic oxygenates is converted to alcohols and at least a portion of said water is reacted with carbon monoxide in said unconverted synthesis gas to produce carbon dioxide and free hydrogen, said second catalyst comprising up to about 10 wt.% of a second alkali metal compound (calculated as the oxide).

23. The process of claim 22 wherein said first catalyst is substantially free of copper.

24. The process of claim 22 wherein said oxidized zinc compound is selected from the group consisting of ZnO and $ZnCO_3$.

25. The process of claim 22 wherein said first alkali metal compound is selected from the group consisting of oxides, hydroxides, and carbonates of an alkali metal selected from the group consisting of potassium, sodium, cesium and rubidium, prior to reduction at operating conditions.

26. The process of claim 25 wherein said first alkali metal compound is selected from the group consisting of $K_2CO_3$ and $Na_2CO_3$.

27. The process of claim 25 wherein said first catalyst is prepared by a method comprising the steps of precipitating said oxidized cobalt as part of a non-stoichiometric complex mixture of one or more of the group consisting of cobalt oxides, hydroxides, and carbonates, washing and drying the resulting precipitate, thereafter impregnating said precipitate with a solution of said first alkali metal compound, drying and optionally calcining said impregnated precipitate to provide a catalytic material.

28. The process of claim 25 wherein said first catalyst is prepared by a method comprising the step of co-precipitating said oxidized cobalt with said first alkali metal compound, followed by washing and drying the resulting precipitate to provide a catalytic material.

29. The process of claim 22 wherein said first catalyst comprises at least about 0.5 wt.% of said first alkali metal compound (calculated as the oxide).

30. The process of claim 22 wherein said first catalyst comprises between about 5 wt.% and 15 wt. zinc (calculated as ZnO).

31. The process of claim 22 wherein said second catalyst additionally comprises ZnO.

32. A process for converting synthesis gas comprising a mixture of $H_2$ and CO to alcohols having at least 2 carbon atoms per molecule, said process comprising the steps of:
   (a) contacting said synthesis gas with a first catalyst comprising an active alkali metal-containing synthesis gas conversion catalyst comprising a major weight proportion of oxidized and metallic cobalt (calculated as CoO) and a minor amount of an oxidized zinc compound under synthesis gas conversion conditions including a temperature of at least about 450° F. to about 650° F. and a pressure of at least about 500 psig to produce an effluent comprising unconverted synthesis gas, water, and unsaturated organic oxygenates having two or more carbon atoms per molecule, said first catalyst comprising from about 50 wt.% to less than 100 Wt.% cobalt (calculated as CoO), 0 to about 20 wt.% oxidized zinc (calculated as ZnO), and up to about 10 wt.% of a first alkali metal compound (calculated as the oxide), selected from the group consisting of oxidized forms of potassium or sodium, the weight ratio of zinc to cobalt being in the range of 0 to about 0.15, calculated as ZnO and CoO, respectively, said percentages being based on the total of said oxidized cobalt, oxidized zinc, and said first alkali metal compound prior to reduction under operating conditions; and
   (b) contacting said effluent with a substantially cobalt-free second catalyst comprising an alkali metal- and copper-containing catalyst having hydrogenation and water-gas shift activity under selective hydrogenation conditions including a temperature in the range of about 400° F. to about 650° F. and a pressure of at least about 500 psig such that a portion of said unsaturated organic oxygenates is converted to alcohols and at least a portion of said water is reacted with carbon monoxide in said unconverted synthesis gas to produce carbon dioxide and free hydrogen, said second catalyst comprising a mixed copper-chromium oxide containing ZnO and up to about 10 wt.% of a second alkali metal compound (calculated as the oxide).

33. The process of claim 32 wherein said first alkali metal compound is selected from the group consisting of $K_2CO_3$ and $Na_2CO_3$.

34. The process of claim 32 wherein said oxidized zinc compound of said first catalyst is selected from the group consisting of ZnO and $ZnCO_3$.

35. The process of claim 32 wherein said first catalyst is prepared by a method comprising the steps of precipitating said oxidized cobalt as part of a non-stoichiometric complex mixture of one or more of the group consisting of cobalt oxides, hydroxides, and carbonates, washing and drying the resulting precipitate, thereafter impregnating said precipitate with a solution of said first alkali metal compound, drying and optionally calcining said impregnated precipitate to provide a catalytic material.

36. The process of claim 32 wherein said first catalyst is prepared by a method comprising the step of coprecipitating said oxidized cobalt with said first alkali metal compound of said first catalyst, followed by washing and drying the resulting precipitate to provide a catalytic material.

37. The process of claim 32 wherein said mixed copper-chromium oxide is a copper chromite material.

38. The process of claim 37 wherein said second catalyst is prepared by a method comprising the steps of:
   (a) coprecipitating Cu(II) ions with chromate ions in the presence of an excess of ammonium relative to copper to produce a copper-ammonium-chromate precipitate;
   (b) drying said copper-ammonium-chromate precipitate to produce a brown product;
   (c) calcining said brown product at a sufficiently high temperature to produce a stable black copper chromite catalyst, said temperature being insufficiently high to degrade said black copper chromite catalyst;
   (d) impregnating said black copper chromite catalyst with a solution of an alkali metal compound; and,
   (e) drying said alkali metal-impregnated copper chromite catalyst.

39. The process of claim 38 wherein said second alkali metal compound of said second catalyst is selected from the group consisting of $K_2CO_3$ and KOH.

40. A process for converting synthesis gas comprising a mixture of $H_2$ and CO to alcohols having at least 2 carbon atoms per molecule, said process comprising the steps of:
   (a) contacting said synthesis gas with a first catalyst comprising an active alkali metal-containing synthesis gas conversion catalyst comprising a major weight proportion of cobalt (calculated as CoO) under synthesis gas conversion conditions to produce an effluent comprising unconverted synthesis gas, water, and unsaturated organic oxygenates having two or more carbon atoms per molecule; and,
   (b) contacting said effluent with a substantially cobalt-free second catalyst comprising a copper-containing hydrogenation catalyst having water-gas shift activity under selective hydrogenation conditions including a temperature of at least about 400° F. such that at least a portion of said unsaturated organic oxygenates is converted to alcohols and at least a portion of said water is reacted with carbon monoxide in said unconverted synthesis gas to produce carbon dioxide and free hydrogen.

41. The process of claim 40 wherein said mixed copper-chromium oxide is a copper chromite material.

42. The process of claim 41 wherein said second catalyst is prepared by a method comprising the steps of:
   (a) coprecipitating Cu(II) ions with chromate ions in the presence of an excess of ammonium relative to copper to produce a copper-ammonium-chromate precipitate;
   (b) drying said copper-ammonium-chromate precipitate to produce a brown product;
   (c) calcining said brown product at a sufficiently high temperature to produce a stable black copper chromite catalyst, said temperature being insufficiently high to degrade said black copper chromite catalyst;
   (d) impregnating said black copper chromite catalyst with a solution of said second alkali metal compound; and,
   (e) drying said alkali metal-impregnated copper chromite catalyst.

43. The process of claim 42 wherein said second catalyst comprises up to about 10 wt.% of an alkali metal compound (calculated as the oxide).

44. The process of claim 42 wherein said alkali metal compound is selected from the group consisting of $K_2CO_3$ and KOH.

45. A process for converting synthesis gas comprising a mixture of $H_2$ and CO to alcohols having at least 2 carbon atoms per molecule, said process comprising the steps of:
   (a) contacting said synthesis gas with a first catalyst comprising an active alkali metal-containing synthesis gas conversion catalyst comprising a major weight proportion of cobalt (calculated as CoO) and a minor amount of oxidized zinc compound under synthesis gas conversion conditions including a temperature of at least about 450° F. and a pressure of at least about 500 psig to produce an effluent comprising unconverted synthesis gas, water, and unsaturated organic oxygenates having two or more carbon atoms per molecule, said first catalyst comprising from about 50 wt.% to less than 100 wt.% cobalt (calculated as CoO), 0 to about 20 wt.% oxidized zinc (calculated as ZnO), and up to about 10 wt.% of a first alkali metal compound (calculated as the oxide), the weight ratio of zinc to cobalt being in the range of 0 to about 0.15, calculated as ZnO and CoO, respectively, said percentages being based on the total of said oxidized cobalt, oxidized zinc, and said first alkali metal compound prior to reduction under operating conditions; and
   (b) contacting said effluent with a substantially cobalt-free second catalyst comprising an alkali metal-containing catalyst comprising a mixed copper-chromium oxide prior to reduction at operating conditions and have hydrogenation and water-gas shift activity under selective hydrogenation conditions including a temperature of at least about 400° F. and a pressure of at least about 500 psig such that a portion of said unsaturated organic oxygenates is converted to alcohols and at least a portion of said water is reacted with carbon monoxide in said unconverted synthesis gas to produce carbon dioxide and free hydrogen, said second catalyst comprising up to about 10 wt.% of a second alkali metal compound (calculated as the oxide).

46. The process of claim 45 wherein said mixed copper-chromium oxide is a copper chromite material.

47. The process of claim 46 wherein said second catalyst is prepared by a method comprising the steps of:
   (a) coprecipitating Cu(II) ions with chromate ions in the presence of an excess of ammonium relative to copper to produce a copper-ammonium-chromate precipitate;
   (b) drying said copper-ammonium-chromate precipitate to produce a brown product;

(c) calcining said brown product at a sufficiently high temperature to produce a stable black copper chromite catalyst, said temperature being insufficiently high to degrade said black copper chromite catalyst;

(d) impregnating said black copper chromite catalyst with a solution of said second alkali metal compound; and, (e) drying said alkali metal-impregnated copper chromite catalyst.

48. The process of claim 47 wherein said second alkali metal compound of said second catalyst is selected from the group consisting of $K_2CO_3$ and KOH.

* * * * *

UNITED STATES PATENT AND TRADEMARK OFFICE
CERTIFICATE OF CORRECTION

PATENT NO. : 5,096,688
DATED : March 17, 1992
INVENTOR(S) : Jeffrey T. Miller, Ceclia A. Radlowski It is certified that error appears in the above-indentified patent and that said Letters Patent is hereby corrected as shown below:

| COL. | LINE | |
|---|---|---|
| 10 | 60 | After "wt." insert --%.-- |
| 17 | 19 | Replace "Nz(NO$_3$)$_2$·6H$_2$O" with --Zn(NO$_3$)$_2$·6H$_2$O-- |
| 18 | 61 | Replace "45.1" with --46.1-- |
| 20 | 50 | After "wt." insert --%-- |
| 20 | 59 | After "compound" insert --(calculated as the oxide)-- |
| 22 | 21 | Delete "said" |
| 22 | 22 | After "active" should read -- substantially copper-free --. |
| 22 | 27-28 | Delete "at least" |
| 22 | 32 | After "molecule," delete --said-- |
| 22 | 35-36 | Replace "up to about 10" with --between about 5 to 15-- |
| 23 | 30 | Replace "an" with -- "said second"--. |
| 23 | 50-51 | Delete "copper-containing" |
| 23 | 51 | After "catalyst" insert --comprising a mixed copper-chromium oxide prior to reduction at operating conditions and-- |
| 24 | 7 | Replace "said second" with --an-- |
| 24 | 25 | Prior to "cobalt" insert --oxidized and metallic-- |
| 24 | 26 | Prior to "oxidized zinc compound" insert --an-- |
| 24 | 48 | Replace "have" with --having-- |

Signed and Sealed this

Thirteenth Day of July, 1993

Attest:

MICHAEL K. KIRK

Attesting Officer   Acting Commissioner of Patents and Trademarks